(12) United States Patent
Fan

(10) Patent No.: US 8,673,478 B2
(45) Date of Patent: Mar. 18, 2014

(54) TEMPERATURE DEPENDENT IONIC GATE

(75) Inventor: Qinbai Fan, Chicago, IL (US)

(73) Assignee: Gas Technology Institute, Des Plaines, IL (US)

(*) Notice: Subject to any disclaimer, the term of this patent is extended or adjusted under 35 U.S.C. 154(b) by 928 days.

(21) Appl. No.: 11/702,236

(22) Filed: Feb. 5, 2007

(65) Prior Publication Data
US 2008/0187818 A1 Aug. 7, 2008

(51) Int. Cl.
*H01M 2/14* (2006.01)
*H01M 6/04* (2006.01)

(52) U.S. Cl.
USPC ............ 429/129; 429/247; 429/249; 429/255

(58) Field of Classification Search
None
See application file for complete search history.

(56) References Cited

U.S. PATENT DOCUMENTS

| | | | |
|---|---|---|---|
| 3,787,240 A * | 1/1974 | Gillman et al. | 429/145 |
| 6,562,519 B2 * | 5/2003 | Yamamoto et al. | 429/247 |
| 2003/0129469 A1 | 7/2003 | Sun et al. | |
| 2004/0007688 A1 * | 1/2004 | Awano et al. | 252/62.2 |
| 2005/0074674 A1 * | 4/2005 | Boone et al. | 429/247 |
| 2005/0260486 A1 | 11/2005 | Cho et al. | |
| 2005/0271941 A1 | 12/2005 | Bushong et al. | |

FOREIGN PATENT DOCUMENTS

JP 63278502 11/1988

* cited by examiner

*Primary Examiner* — Cynthia K. Walls
(74) *Attorney, Agent, or Firm* — Pauley Peterson & Erickson

(57) ABSTRACT

An electrochemical device having a liquid electrolyte which includes a protic solvent, an anode electrode disposed in contact with the liquid electrolyte, and a cathode electrode disposed in contact with the liquid electrolyte. A membrane which interrupts the transport of ions between the electrodes at a predetermined temperature is disposed in the liquid electrolyte between the anode electrode and the cathode electrode. In this way, electrochemical devices such as batteries, fuel cells, electrolyzers, and sensors, which may overheat during use and cause a fire or explosion, are precluded from overheating.

8 Claims, 2 Drawing Sheets

TEMPERATURE DEPENDENT IONIC GATE

BACKGROUND OF THE INVENTION

1. Field of the Invention

This invention relates to electrochemical devices which employ liquid electrolytes. More particularly, this invention relates to electrochemical cells which generate electricity, such as batteries, fuel cells, and electrolyzers. This invention further relates to a method and means for preventing fire and explosion hazards associated with such devices.

2. Description of Related Art

An electrochemical cell is a device in which a chemical reaction is used as a source of energy to generate an electric current. These devices generally comprise an anode electrode, a cathode electrode, and an electrolyte disposed between the two electrodes. Certain of these devices utilize ionic conduction in a liquid electrolyte, e.g. liquid solutions and molten salts, to generate the desired electric current.

In recent history, there have been a number of instances of fires and explosions caused by overheated storage batteries. Other electrochemical devices are also prone to such hazards. However, such hazards can be avoided by shutting down the electrochemical device before the device reaches a critical state, for example, a predetermined temperature. U.S. Patent Application Publication No. 2005/0260486 A1 teaches a battery having a safety element connected between its positive and negative electrodes, which safety element comprises material having a Metal-Insulator Transition (MIT) characteristic where the resistance abruptly drops at or above a certain temperature. The material senses the rise of battery temperature and lowers the charged state of the battery when the battery is exposed to an elevated temperature, the battery temperature rises due to external impact by pressure, nails or nippers, the battery temperature rises due to increases in ambient temperature, or the battery temperature rises due to overcharging. The MIT characteristic is indicated to be a material-specific characteristic which is presented only by materials including vanadium-based oxides, $Ti_2O_3$, or materials to which an element such as St, Ba, La, etc. is added, where resistance of the materials abruptly changes according to temperature. The change in resistance is indicated to be caused by a phase transition of a crystalline structure between a metal and an insulator. By use of materials having the disclosed MIT characteristic, the battery is turned into a stable discharged state at elevated temperatures.

SUMMARY OF THE INVENTION

It is one object of this invention to provide a method and means for preventing fires or explosions associated with electrochemical devices having liquid electrolytes.

This and other objects of this invention are addressed by an electrochemical device comprising a liquid electrolyte comprising a protic solvent, an anode electrode disposed in contact with the liquid electrolyte, a cathode electrode disposed in contact with the liquid electrolyte, and ion transport interruption means for interrupting transport of ions between the electrodes at a predetermined temperature disposed in the liquid electrolyte between the two electrodes. In accordance with one preferred embodiment of this invention, the ion transport interruption means comprises a temperature dependent ion-permeable membrane which stops the flow of ions, cations or anions, in the electrochemical device when the temperature of the electrochemical device reaches a hazardous level. The mechanism of the temperature dependent ion permeable membrane is the use of the membrane temperature-dependent wettability (solubility) to allow or stop ion transport between the electrodes. Thus, when the temperature of the electrochemical device reaches a predetermined high point, the membrane wettability becomes substantially zero as a result of which the ions cannot transport through the membrane because the ion transport is dependent upon the solution permeability/pressure. Solution permeability is a measure of the rate at which a solution will move through a medium. When the pressure increases, the permeability increases. Ionic salts dissolve in the solution. If there is no solution permeability, there is no ionic conductivity.

BRIEF DESCRIPTION OF THE DRAWINGS

These and other objects and features of this invention will be better understood from the following detailed description taken in conjunction with the drawings, wherein.

DETAILED DESCRIPTION OF THE PRESENTLY PREFERRED EMBODIMENTS

Figure 1:
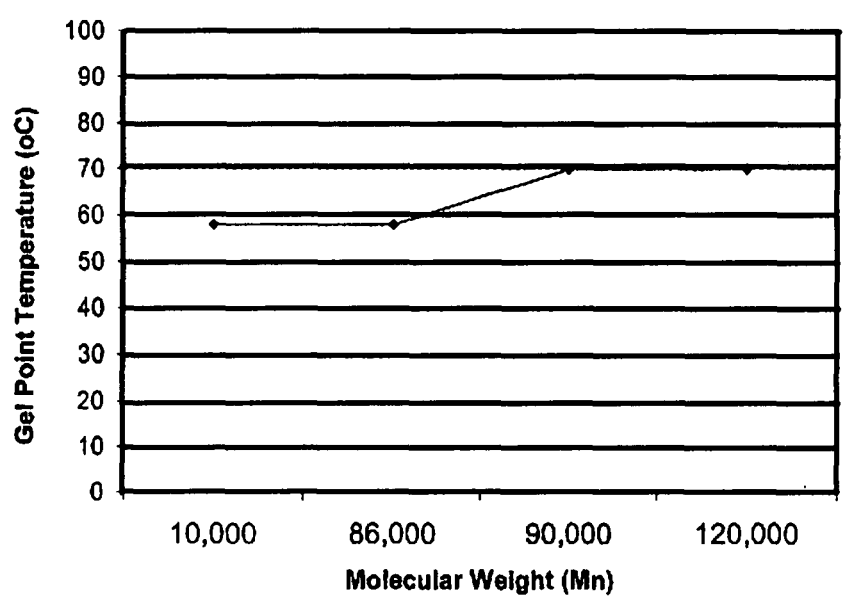
FIG. 1 is a diagram showing the gel temperature of hydroxypropylmethyl cellulose versus molecular weight.

This invention involves the use of a membrane material that shuts down or interrupts the flow of ions at high temperatures in liquid electrolyte solutions. This temperature dependent ion "gate" material has a property of temperature-dependent wettability. When the membrane material exhibits wettability, e.g. in a gel-type material membrane, the membrane is ion permeable and the ions pass through the membrane; but when the membrane exhibits no wettability, the membrane is ion impermeable and the ions are unable to permeate through the membrane, effectively shutting down the flow of ions.

The invention will now be described herein as it relates to the transport of hydroxyl ions in aqueous alkaline solutions. However, it is to be understood that the invention is applicable to membrane materials having temperature-dependent wettability in any electrolyte comprising a protic solvent, and such membrane materials are deemed to be within the scope of this invention. It will also be understood that, as used herein, the term "ion" refers to both cations and anions.

In accordance with one embodiment of this invention, the invention comprises a membrane material which shuts down the transport of hydroxyl ions at high temperatures in concentrated caustic solutions. This temperature-dependent hydroxyl "gate" membrane material has the characteristic of temperature-dependent wettability (solubility). When the material is at a temperature at which it exhibits wettability, the hydroxyl ions pass through the material. However, when the material is at a temperature at which it exhibits no wettability, the material becomes hydroxyl-ion impermeable, thereby preventing the flow of hydroxyl ions from one side to the other side of the membrane.

In accordance with one embodiment of this invention, the membranes having temperature-dependent wettability comprise materials comprising cellulosic groups, which groups exhibit temperature-dependent wettability in water. As the temperature increases, the wettability decreases. Exemplary of a cellulosic material suitable for use in the electrochemical devices of this invention is synthesized polyhydroxypropyl cellulose. Cellulosic materials are stable in caustic solutions and are reversible for hydroxyl transport and transport interruption.

Polyhydroxylpropyl cellulose is hydroxyl permeable at temperatures in the range of about −40° C. to about 70° C. and this range may be expandable up to about 150° C. It may be synthesized by reaction of cellulose with polypropylene oxide in the presence of an alkaline agent, such as sodium hydroxide. Polyhydroxylpropyl cellulose is a nonionic polymer which is wettable (soluble) in water and polar organic solvents. The ionic permeability is proportional to the water permeability. The wettability, or temperature-dependency, may be tuned by using different copolymers, such as polyvinyl alcohol, and cross-linking agents, such as glutaraldehyde to produce the membrane materials. This material can even be made to be stable in hot water.

FIG. 1 is a diagram showing the relationship between the gel temperature of a material suitable for use in this invention, hydroxylpropylmethyl cellulose, and its molecular weight. As shown therein, the gel point temperature, i.e. the temperature at which the material becomes unwettable, increases with increases in molecular weight. Thus, adjusting the molecular weight of a material suitable for use in this invention can be used to adjust the temperature at which the material becomes unwettable, thereby enabling the use of the material over a wide temperature range. This, in turn, enables the use of the material in a broad range of applications having different critical operating temperatures.

Figure 2:
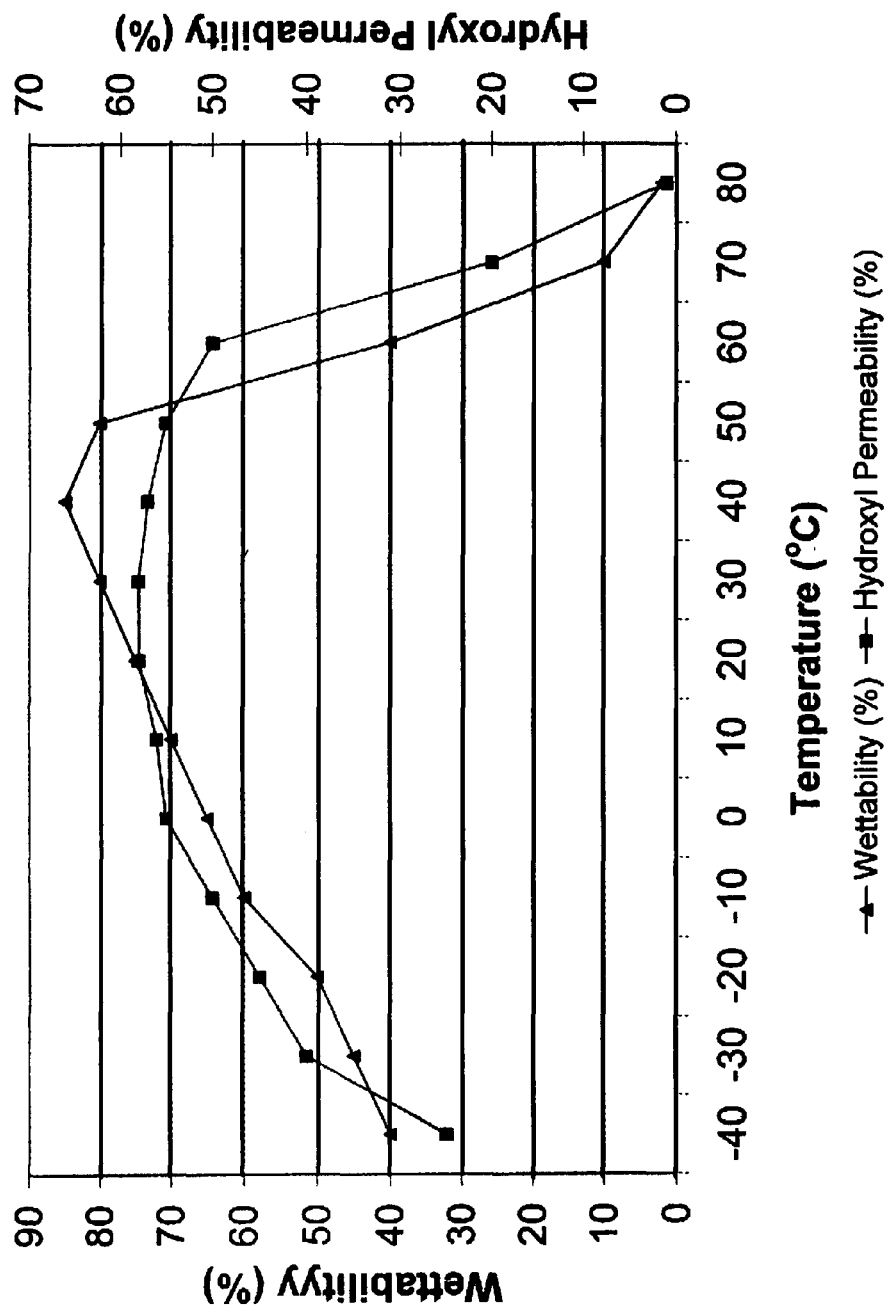
FIG. 2 is a diagram showing hydroxyl ion permeability and membrane wettability at various temperatures.

FIG. 2 is a diagram showing hydroxyl ion permeability and membrane wettability as a function of temperature for hydroxylpropylmethyl cellulose. As shown therein, when the temperature of the cellulosic material reaches about 80° C., the material becomes substantially unwettable and the hydroxyl ion permeability becomes very low, effectively shutting down the heat-producing reactions.

The membranes of this invention comprising a temperature-dependent ion permeable material may be utilized in batteries, fuel cells, electrolyzers, ion-conducting sensors, and ionic switches.

EXAMPLE 1

In this example, a membrane having temperature-dependent ion permeability is produced by mixing 10 g of hydroxypropyl methyl cellulose (Aldrich-Sigma Chemicals) with 10 g of polypropylene oxide in a 0.1M NaOH solution. The solution is then film cast to form a membrane and dried at 80° C. for one hour. This membrane is crosslinked and stable in water.

EXAMPLE 2

In this example, a membrane having temperature-dependent ion permeability is produced by mixing 10 g of hydroxypropyl methyl cellulose with 10 g of polypropylene oxide and 10 g PVOH in a 0.1M NaOH solution. This solution is film cast to form a membrane and dried at 40° C. to remove water. The membrane is then dipped into a 20% by weight glutaraldehyde 1M HCl solution for crosslinking. The resulting membrane is dried at 80° C. The use of glutaraldehyde as a cross-linking agent produces a membrane which is both strong and unwettable in hot water.

While in the foregoing specification this invention has been described in relation to certain preferred embodiments thereof, and many details have been set forth for the purpose of illustration, it will be apparent to those skilled in the art that the invention is susceptible to additional embodiments and that certain of the details described herein can be varied considerably without departing from the basic principles of this invention.

What is claimed is:

1. In an electrochemical device having a liquid electrolyte, an anode electrode disposed in contact with said liquid electrolyte, and a cathode electrode disposed in contact with said liquid electrolyte, a method for preventing a fire or explosion in said electrochemical device, said method comprising:
inserting a membrane comprising hydroxylpropylmethyl cellulose into said liquid electrolyte between said anode electrode and said cathode electrode, the membrane adapted to interrupt transport of ions between said electrodes at a temperature in a range of about −40° C. to about 150° C. and wherein adjusting the molecular weight of the hydroxylpropylmethyl cellulose adjusts said temperature at which the membrane interrupts said transport of ions.

2. A method in accordance with claim 1, wherein said electrolyte comprises a protic solvent.

3. A method in accordance with claim 1, wherein said hydroxylpropylmethyl cellulose is cross-linked.

4. A method in accordance with claim 3, wherein said hydroxylpropylmethyl cellulose is cross-linked using glutaraldehyde as a cross-linking agent.

5. A method in accordance with claim 1, wherein said electrochemical device is selected from the group consisting of a battery, a fuel cell, an electrolyzer, a sensor, and an ionic switch.

6. A method in accordance with claim 1, wherein said membrane additionally comprises polyvinyl alcohol copolymer.

7. A method in accordance with claim 1, wherein said membrane permits transport of ions between said electrodes at a temperature in a range of about 70° C. to about 150° C.

8. A method in accordance with claim 1, wherein said membrane permits transport of ions between said electrodes at a temperature in a range of about 80° C. to about 150° C.

* * * * *